United States Patent
Denis

(10) Patent No.: US 6,664,398 B2
(45) Date of Patent: Dec. 16, 2003

(54) DERIVATIVES OF ERYTHROMYCIN, THEIR PREPARATION PROCESS AND THEIR USE AS MEDICAMENTS

(75) Inventor: Alexis Denis, Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 10/188,394

(22) Filed: Jul. 2, 2002

(65) Prior Publication Data

US 2003/0050254 A1 Mar. 13, 2003

Related U.S. Application Data

(62) Division of application No. 09/442,681, filed on Nov. 18, 1999, now Pat. No. 6,440,941.

(51) Int. Cl.$^7$ ............................................. C07D 293/00
(52) U.S. Cl. ........................... 548/100; 544/1; 544/184
(58) Field of Search ............................ 546/185, 1, 184; 548/100

(56) References Cited

U.S. PATENT DOCUMENTS 6,100,404 A * 8/2000 Agouridas et al. ........ 546/272.7
6,440,941 B1 * 8/2002 Denis ........................... 514/29

* cited by examiner

*Primary Examiner*—Elli Peselev
(74) *Attorney, Agent, or Firm*—Muserlian, Lucas and Mercanti

(57) ABSTRACT

A subject of the invention is the compounds of formula

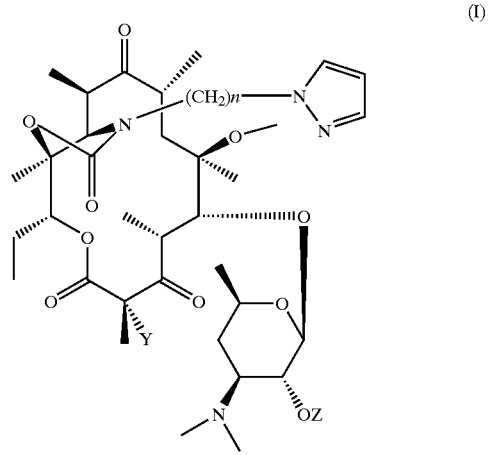

(I)

in which
  Y represents a hydrogen atom or a fluorine atom,
  n represents an integer comprised between 1 and 8,
  Z represents a hydrogen atom or the remainder of a carboxylic acid, optionally substituted on the heterocycle by one or more alkyl, alkenyl, alkynyl, O-alkyl, O-alkenyl, O-alkynyl, S-alkyl, S-alkenyl, S-alkynyl radicals containing up to 8 carbon atoms, one or more OH, $NH_2$, C=N, $NO_2$, $CF_3$ radicals or one or more aryl radicals containing up to 14 carbon atoms or heteroaryl radicals containing one or more nitrogen oxygen or sulphur atoms, the aryl or heteroaryl radicals themselves being able to be substituted as well as their addition salts with acids, The products of formula (I) have antibiotic properties.

3 Claims, No Drawings

DERIVATIVES OF ERYTHROMYCIN, THEIR PREPARATION PROCESS AND THEIR USE AS MEDICAMENTS

This application is a division of U.S. patent application Ser. No. 09/442,681 filed Nov. 18, 1999, now U.S. Pat. No. 6,440,941 B1.

The present invention relates to new derivatives of erythromycin, their preparation process and their use as medicaments.

A subject of the invention is the compounds of formula (I)

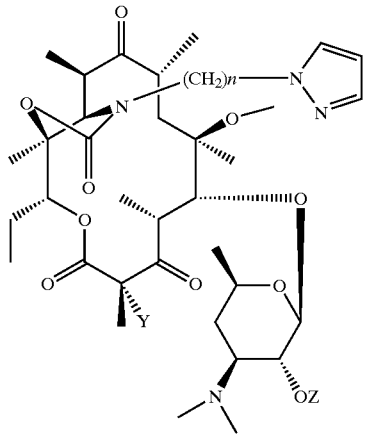

(I)

in which
- Y represents a hydrogen atom or a fluorine atom,
- n represents an integer comprised between 1 and 8,
- Z represents a hydrogen atom or the remainder of a carboxylic acid,
- optionally substituted on the heterocyle by one or more alkyl, alkenyl, alkynyl, O-alkyl, O-alkenyl, O-alkynyl, S-alkyl, S-alkenyl, S-alkynyl radicals containing up to 8 carbon atoms, one or more OH, $NH_2$, C=N, $NO_2$, $CF_3$ radicals or one or more aryl radicals containing up to 14 carbon atoms or heteroaryl radicals containing one or more nitrogen oxygen or sulphur atoms, the aryl or heteroaryl radicals themselves being able to be substituted as well as their addition salts with acids.

As an example of the addition salts of the present derivatives with mineral or organic acids, the salts formed with acetic, propionic, trifluoroacetic, maleic, tartaric, methanesulphonic, benzenesulphonic, p-toluenesulphonic, hydrochloric, hydrobromic, hydroiodic, sulphuric, phosphoric acids and especially stearic, ethylsuccinic or laurylsulphonic acids can be mentioned.

In the definition of the substituants, the alkyl, alkenyl or alkynyl radical is preferably a methyl, ethyl, propyl, isopropyl, n-butyl, isobutyl, terbutyl, decyl or dodecyl, vinyl, allyl, ethynyl, propynyl, propargyl, cyclobutyl, cyclopentyl or cyclohexyl radical.

The aryl radical can be a phenyl or naphthyl radical.

The substituted or non substituted heteroaryl radical can be a thienyl, furyl, pyrolyl, thiazolyl, oxazolyl, imidazolyl, thiadiazolyl, pyrazolyl or isopyrazolyl radical, a pyridyl, pyrimidyl, pyridazinyl or pyrazinyl radical or also an indolyl, benzofurannyl, benzothiazyl or quinolinyl radical. These aryl radicals can contain one or more substituants chosen from the groups mentioned above.

A quite particular subject of the invention is the compounds of formula (I) in which Z represents a hydrogen atom, those in which n represents the number 4, those in which the

radical is substituted by a

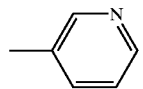

radical.

A more particular subject of the invention is the compounds of formula (I) in which Y represents a hydrogen atom.

Among the preferred compounds, the compounds whose preparation is given here after in the experimental part can particularly be mentioned and more particularly the compound of Example 1

The products of general formula (I) have a very good antibiotic activity on gram ⊕ (bacteria such as staphylococci, streptococci, pneumococci.

The compounds of the invention can therefore be used as medicaments in the treatment of germ-sensitive infections and in particular, in that of staphylococcia such as staphylococcal septicaemias, malignant staphylococcia of the face or skin, pyodermitis, septic or suppurating wounds, boils, anthrax, phlegmons, erysipelas and acne, staphylococcia such as primitive or post-influenzal acute angina, bronchopneumonia, pulmonary suppuration, streptococcia such as acute angina, otitis, sinusitis, scarlatina, pneumococcia such as pneumonia, bronchitis, brucellosis, diphtheria, gonococcal infection The products of the present invention are also active against infections caused by germs such as *Haemophilus influenzae*, Rickettsia, *Mycoplasma pneumoniae*, Chlamydia, Legionella, Ureaplasma, Toxoplasma, or germs of the Mycobacterium genus.

Therefore, a subject of the present invention is also the products of formula (I) as defined above, as well as their addition salts with the pharmaceutically acceptable mineral or organic acids, as medicaments and, in particular antibiotic medicaments.

A more particular subject of the invention is the product of Example 1 and its pharmaceutically acceptable salts, as medicaments and, in particular antibiotic medicaments.

A subject of the invention is also the pharmaceutical compositions containing at least one of the medicaments defined above, as active ingredient.

These compositions can be administered by buccal, rectal, parenteral route, or by local route as a topical application on the skin and mucous membranes, but the preferred administration route is the buccal route.

They can be solids or liquids and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated with the excipients usually used in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example, apyrogenic sterile water.

The dose administered is variable according to the affection treated, the patient in question, the administration route and the product considered. It can be, for example, comprised between 50 mg and 3000 mg per day by oral route for an adult for the product of Example 1.

A subject of the invention is also a preparation process characterized in that a compound of formula (II)

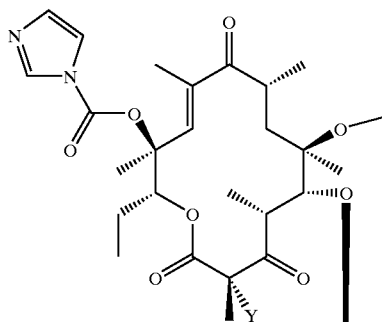

(II)

in which Y retains its preceding meaning and M represents the remainder of an acid is subjected to the action of a compound of formula (III)

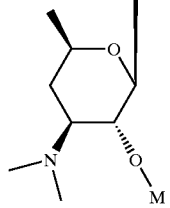

III in which the heterocyclic radical can be substituted in order to obtain the compound of formula (IA) in which Z represents the remainder of an acid, then if desired this compound of formula (IA) is subjected to the action of an agent which releases hydroxyl in position 2' in order to obtain the corresponding compound of formula (IB) in which Z represents a hydrogen atom which if desired is subjected to the action of an acid in order to form the salt, the reaction of the compound of formula (II) with the compound of formula (III) takes place in a solvent such as for example acetonitrile, dimethylformamide or also tetrahydrofuran, dimethoxyethane or dimethylsulphoxide, the hydrolysis of the ester function in position 2' is carried out using methanol or aqueous hydrochloric acid, the salification is carried out using acids according to standard processess.

The compounds of formula (II) in which Y represents a hydrogen atom, used as starting products are described and claimed in the European Patent Application 0 596 802.

The compounds of formula (II) in which Y represents a fluorine atom can be prepared as indicated hereafter in the experimental part.

A subject of the invention is also new chemical products, the compounds of formula (III) and more especially the compound of formula (III) the preparation of which is given hereafter in the experimental part.

EXAMPLE 1

11,12-dideoxy-3-de[(2,6-dideoxy-3-C-methyl-3-O-methyl-.alpha.-L-ribohexopyranosyl)oxy]-6-O-methyl -3-oxo-12,11-[oxycarbonyl[[4-[3-(3-pyridinyl)-1H-pyrazol -1-yl]butyl]imino]]-erythromycin A mixture of 26 cm$^3$ of acetonitrile, 2.5 cm$^3$ of water, 5.13 g of amine prepared hereafter (Preparation 1) and 6.20 g of 2'-acetate and 12-(1H-imidazol-1-ylcarboxylate) of 10,11-didehydro-11-deoxy-3-de[(2,6-dideoxy-3-C-methyl-3-O-methyl-.alpha.-L-ribo-hexopyranosyl) oxy]-6-O-methyl-3-oxo-erythromycin is taken to 55° C. for 21 hours.

The reaction mixture is poured into water, extracted with ethyl acetate and dried. 8.02 g of product is obtained which is placed in 70 cm$^3$ of methanol. The reaction mixture is taken to reflux for 1 hour 30 minutes. The product obtained is chromatographed on silica eluting with a methylene chloride, methanol, ammonium hydroxide mixture 95-5-0.5. 3.59 g of product is obtained melting at 143–145° C.

| NMR CDCl$_3$ ppm | | | |
|---|---|---|---|
| Number | $^1$H | Number | $^1$H |
| 1 | | 1' | 4.28 |
| 2 | 3.86 | 2' | 3.16 |
| 3 | | 3' | 2.44 |
| 4 | 3.07 | 4' | 1.67–1.23 |
| 5 | 4.21 | 5' | 3.52 |
| 6 | | 5' Me | 1.24 |
| 7 | 1.59–1.82 | N(Me)$_2$ | 2.26 |
| 8 | 2.60 | NCH2 | 3.60 to 3.80 |
| 9 | | CH2 | 1.65 |
| 10 | 3.13 | CH2 | 1.95 |
| 11 | 3.57 | CH2N | 4.21 |
| 12 | | Pyrazole H4 | 6.55 |
| 13 | 4.94 | Pyrazole H5 | 7.47 |
| 14 | 1.95–1.57 | pyridine | |
| 15 | 0.85 | H2 | 9.00 |
| 2Me | 1.36 | H4 | 8.11 |
| 4Me | 1.31 | H5 | 7.31 |
| 6Me | 1.33 or 1.47 | H6 | 8.51 |
| 8Me | 1.16 | | |
| 10Me | 1.00 | | |
| 12Me | 1.33 or 1.47 | | |
| 60Me | 2.60 | | |

Preparation 1

3-3-(3-pyridinyl)-1H-pyrazole-1-butanamine

Stage A: 2-[4-[3-(3-pyridinyl)-1H-pyrazol-1-yl]butyl]-1H -isoindole-1,3(2H)-dione 15.45 g of 3-(1H pyrazol-3-yl)-pyridine prepared as indicated in CA 68 P 95812 g (1968) is introduced dropwise over 1 hour while maintaining the temperature below 30° C. or equal to 30° C. into a mixture of 20 ml of DMF and 6.13 g of sodium hydride. A solution of 29.90 g of 2-(4-bromobutyl)-1H -isoindole-1,3(2H)-dione and 110 ml of DMF is added dropwise. The reaction medium is agitated for 30 minutes at ambient temperature, followed by concentrating, pouring into 300 ml of water cooled down to 10° C., extracting with ethyl acetate, washing with water, drying, filtering and concentrating. The residue is taken up in methylene chloride, followed by drying, filtering and concentrating. 35.87 of a product is obtained which is crystallized from ethyl ether, dried, washed with water and dried. 22.93 g of sought product is obtained.

Stage B: 3-(3-pyridinyl)-1H-pyrazole-1-butanamine 7 ml of hydrazine hydrate is added to a suspension containing 450 ml of ethanol and 22.33 g of the product of Stage A. The reaction medium is taken to reflux for 15 hours. The ethanol is evaporated off, the reaction mixture is agitated with 200 ml of ethyl acetate, washed with salt water, dried, filtered and concentrated. In this way 9.60 g of sought product is obtained.

EXAMPLE 2

11,12-dideoxy-3-de[(2,6-dideoxy-3-C-methyl-3-O-methyl-.alpha. -L-ribohexopyranosyl)oxy]2-fluoro -6-O-methyl-3-oxo-12,11-[oxycarbonyl[[4-[3-(3-pyridinyl)-1H-pyrozol-1-yl]butyl]imino]]-erythromycin By operating as previously, starting with the corresponding 2-fluorinated derivative of formula (II) prepared as indicated hereafter, the sought product is obtained M.p.= 117~121° C.

Preparation of the compound of formula (II) in which Y represents a fluorine atom.

2'-acetoxy 2 α-fluoro of 12-(oxycarbonylimidazol)11-deoxy 10,11-didehydro 3-de[(2,6-dideoxy 3-C-methyl 3-O-methyl α-L-ribohexopyranosyl)oxy]6-O-methyl 3-oxo erythromycin.

Stage A: 11-deoxy 10,11-didehydro 3-de[(2,6-dideoxy 3-O -methyl α-L-ribohexopyranosyl) oxy]6-O-methyl 3-oxo erythromycin.

A mixture of 8.722 g of 11-deoxy 10,11-didehydro 3-de [(2,6-dideoxy 3-O-methyl αL-ribohexopyranosyl)oxy]6-O-methyl 3-oxo erythromycin 2'-acetate and 350 ml of anhydrous methanol (EP 596802) is agitated for 44 hours. 8.794 g of the sought product is obtained.

Stage B: 2'-trimethylsilyloxy of 11-deoxy 10,11-didehydro 3-de[(2,6-dideoxy 3-O-methyl α-L-ribohexopyranosyl)oxy] 6-O-methyl 3-oxo erythrmycin A mixture containing 3.08 g of the product of the preceding stage, 340 mg of imidazole, 32 ml of THF anhydride and 1.06 ml of hexamethyldisilylazane is agitated at ambient temperature for 4 days. The reacton medium is evaporated to dryness, then taken up in a mixture of 60 ml of methylene chloride and 60 ml of 0.5 M sodium acid phosphate. The reaction mixture is maintained under agitation for 15 minutes, decanted, extracted with methylene chloride, dried and evaporated to dryness. 3.345 g of the sought product is obtained.

Stage C: 2'-trimethylsilyloxy 2α-fluoro of 11-deoxy 10,11-didehydro 3-de[(2,6-dideoxy 3-O methyl α-L-ribohexo -pyranosyl) oxy]6-O-methyl 3-oxo erthromycin.

1.24 ml of a 0.97M solution of potassium terbutylate in THF is added at −12° C. under an argon atmosphere to a solution containing 668 mg of 2'-trimethylsilyloxy of 11-deoxy 10,11-didehydro 3-de[(2,6-dideoxy 3-O-methyl α-L-ribohexopyranosyl) oxy]6-O-methyl 3-oxo erythromycin and 6.7 ml of anhydrous THF. The reaction medium is agitated for 5 minutes and 378 mg of N-fluoro dibenzene-sulphonimide is added. The reaction medium is agitated for 10 minutes at −12° C. and left to return to ambient temperature for 1 hour 30 minutes. The isolation and purification operations are carried out and 695 mg of the sought product is obtained.

Stage D: 2α-fluoro of 11-deoxy 10,11-didehydro 3-de[(2,6-dideoxy 3-O-methyl 3-O-methyl α-L-ribohexopyranosyl) oxy]6-O-methyl 3-oxo erythromycin A mixture of 5.476 g of product of Example 2, 50 ml of THF and 11.2 ml of 1M tetrabutylammonium fluoride in THF is agitated for 3 hours 30 minutes. The solvent is evaporated off and 37 ml of ethyl acetate, 37 ml of water and 7.5 ml of 20% ammonium hydroxide are added. The reaction medium is agitated for 10 minutes, decanted, extracted with ethyl acetate, dried, filtered and the filtrate is concentrated to dryness. The product obtained is chromatographed on silica eluting with an ammoniated $CH_2CL_2$-MeOH mixture 99-1, then 98-2, 97-3, 96-4, 95-5. 2.452 g of sought product is obtained.

Stage E: 2'-acetoxy 2α-fluoro of 11-deoxy 10,11-didehydro 3-de [(2,6-dideoxy 3-O-methyl α-L-ribohexopyranosyl) oxy]6-O-methyl 3-oxo erythromycin 1.02 g of the product of Stage A, 10 ml of methylene chloride and 241 μl of acetic anhydride are maintained under agitation for 3 hours. After evaporation 10 ml of water and 10 ml of ethyl acetate are added. The reaction medium is left for 1 hour under agitation at an ambient temperature, decanted, dried and evaporated. 1.01 g of sought product is obtained.

Stage F: 2'-acetoxy 2α-fluoro of 12-(oxycarbonylimidazol) 11-deoxy 10,11-didehydro 3-de[(2,6-dideoxy 3-C-methyl-3-O-methyl α-L-ribohexopyranosyl)oxy]6-O-methyl 3-oxo erythromycin 0.388 g of carbonyldiimidazole and 24 μL of DBU are added at 0° C. to a solution containing 1.01 g of the product of the preceding stage and 10 ml of anhydrous THF. The THF is evaporated off and 10 ml of water and 10 ml of ethyl acetate are added. The reaction mixture is maintained under agitation for 10 minutes, extracted, dried and evaporated. 0.902 g of crude sought product is obtained which is chromatographed eluting with an ethyl acetate-triethylamine mixture 96-4. 0.573 g of sought product is obtained.

EXAMPLE 3

By operating as in Example 1 using 4-(3-pyridinyl)-1H-pyrazole-1-butanamine, 11,12-dideoxy-3-de[(2,6-dideoxy-3-C-methyl-3-O-methyl-.alpha. -L-ribohexopyranosy)oxy]-6-O-methyl-3-oxo-12,11-[oxycarbonyl[[4-[4-(3-pyridinyl)-1H-pyrazol-1-yl ]butyl]-imino]]-erythromycin is obtained.

Mass spectrum $MH^+=812^+$

NMR spectrum (300MHz in $CDCl_3$)

H2: 3.84 ppm; H4: 3006 ppm; H5: 4.22 ppm; H7: 1.58 1.83 ppm; H8: 2.58 ppm; H10: 3.12 ppm; H11: 3.56 ppm; H13: 4.92 ppm; H14: 1.55 1.94; H15: 0.81 ppm; 2Me: 1.35 ppm; 4Me 1.29 ppm; 6 Me: 1.32 or 1.46 ppm; 8 Me 1.16 ppm; 10 Me: 1.01 ppm; 12 Me: 1.32 or 1.46 ppm; 60 Me: 2.6 ppm; 1': 4.27 ppm; 2': 3.17 ppm; 3'2.44 ppm; 4': 1.67 and 1.24 ppm; 5': 3.55 ppm; $Nme_2$: 2.26 ppm; $NCH_2$: 3.69 ppm; $CH_2$: 1.64 1.94 ppm; $CH_2N$: 4.19 ppm; pyrazole: 7.77 ppm; pyridine: 8.76 7.75 7.27 8.44 ppm.

Mass spectrum $812^+$: $MH^+$ $850^+$: MK+

The starting amine was prepared as in Preparation 1 starting with the product prepared as indicated in the following diagram.

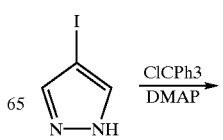

-continued

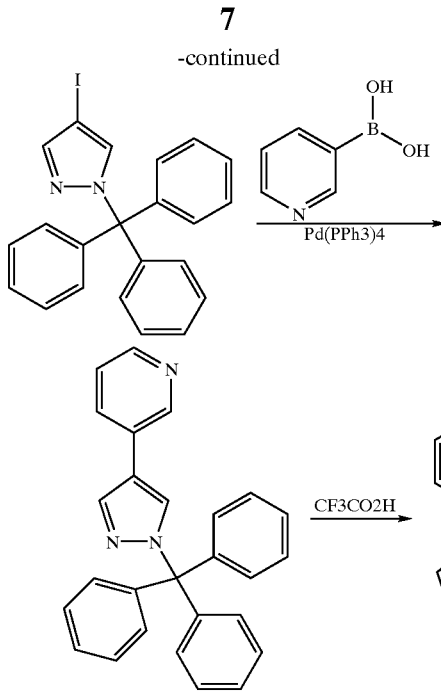

EXAMPLE 4

11,12-dideoxy-3-de[(2,6-dideoxy-3-C-methyl-3-O-methyl-.alpha.-L-ribohexopyranosyl)oxy]-2-fluoro-3-oxo-12,11-[oxycarbonyl[(4-[4-(3-pyridinyl)-1H-pyrazol-1-yl]butyl]-imino]]-erythromycin NMR spectrum (300 MHz in CDCl3) H4: 3.53 ppm; H5: 4.05 ppm; H7: 1.51 1.88 ppm; H8: 2.61 ppm; H10: 3.10 ppm; H11: 3.42 ppm; H13: 4.86 ppm; H14: 1.63 1.95; H15: 0.85 ppm; 2Me: 1.75 ppm; 4Me: 1.29 ppm; 6 Me: 1.31 or 1.49 ppm; 8Me: 1.17 ppm; 10Me: 1.00 ppm; 12Me: 1.31 or 1.49 ppm; 6OMe: 2.51 ppm; 1': 4.30 ppm; 2': 3.19 ppm; 3': 2.48 ppm; 4': 1.68 and 1.26 ppm; 5': 3.53 ppm; 5' Me: 1.24 ppm; Nme$_2$: 2.28 ppm; NCH$_2$: 3.55 to 3.80 ppm; CH$_2$: 1.61 1.93 ppm; CH$_2$N: 4.19 ppm; pyrazole: 7.75 7.78 ppm; pyridine: 8.77 7.77 7.27 8.44 ppm Mass spectrum

830$^+$: MH$^+$

158$^+$: Desosamine

673$^+$: 830$^+$-158$^+$H

EXAMPLES OF PHARMACEUTICAL COMPOSITION

Tablets containing the following were prepared:

| Product of Example 1 | 150 mg |
|---|---|
| Excipient s.q.f. | 1 g |

Detail of excipient: starch, talc, magnesium stearate

Pharmacological Study of the Products of the Invention

Method of dilutions in liquid medium A series of tubes is prepared in which the same quantity of nutritive sterile medium is distributed. Increasing quantities of the product to be studied are distributed into each tube, then each tube is sown with a bacterial strain. After incubation for twenty-four hours in a heating chamber at 37° C., the growth inhibition is evaluated by transillumination, which allows the minimal inhibitory concentrations (M.I.C.) to be determined, expressed in micrograms/cm$^3$. The following results were obtained with the product of Example 1: (reading after 24 hours)

| Bacterial strains GRAM$^+$ | | |
|---|---|---|
| S. aureus | 011UC4 | 0.040 |
| S. aureus | 011UC4+ 50% serum | 0.600 |
| S. aureus | 011B18c | |
| S. aureus | 011GR12c | |
| S. aureus | 011GO25i | 0.600 |
| S. epidermidis | 012GO11i | 0.040 |
| S. aureus | 011CB20c | |
| S. epidermidis | 012GO40c | |
| S. pyogenes | 02A1UC1 | 0.02 |
| S. agalactiae | 02B1HT1 | 0.02 |
| S. faecalis | 02D2UC1 | 0.02 |
| S. faecium | 02D3HT1 | 0.02 |
| Streptococcus gr.G | 02GOGR5 | 0.02 |
| S. mitis | 02MitCB1 | 0.02 |
| S. agalactiae | 02B1SJ1c | 0.050 |
| S. faecalis | 02D2DU15c | 5.000 |
| Streptococcus gr.G | 02Gogr4c | |
| S. sanguis | 02SGr10i | 0.02 |
| S. mitis | 02MitGR16i | 0.02 |
| S. pneumoniae | 032UC1 | 0.02 |
| S. pneumoniae | 030GR20 | 0.02 |
| S. pneumoniae | 030SJ5i | 0.040 |
| S. pneumoniae | 030CR18c | 0.300 |
| S. pneumoniae | 030PW23c | 0.02 |
| S. pneumoniae | 030RO1i | 0.150 |
| S. pneumoniae | 030SJ1c | 0.150 |

Moreover, the product of Example 1 in particular shows a useful activity on the following gram$^{30}$ bacterial strains: Haemophilus Influenzae 351HT3, 351CB12, 351CA1 and 351GR6.

What I claim is:

1. A compound of the formula

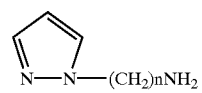

III wherein n is an integer from from 1 to 8, which may be substituted with

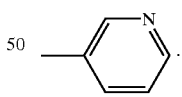

.

2. A compound of claim 1 which is 3-(3-pyridinyl)-1H-pyrazole-1-butanamine or 4-(3-pyridinyl)-1H-pyrazole-1-butanamine.

3. A compound of the formula

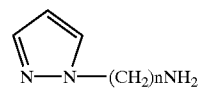

III wherein n is an iteger from 1 to 8, unsubstituted or substituted on the heterocycle by at least one member selected from the group consisting of alkyl, alkenyl, alkynyl, O-alkyl, O-alkenyl, O-alkynyl, S-alkyl, S-alkenyl, S-alkynyl of up to 8 carbon atoms, —OH, —NH$_2$, —C≡N, —NO$_2$, —CF$_3$, one or more aryl radicals containing up to 14 carbon atoms or heteroalyl having at least one member of the group consisting of nitrogen, oxygen and sulfur, the aryl or heteroaryl themselves being able to be substituted.

* * * * *